(12) United States Patent  (10) Patent No.: US 6,988,993 B2
Sullivan et al.  (45) Date of Patent: Jan. 24, 2006

(54) BIOPHYSICAL SENSOR

(75) Inventors: Colin Edward Sullivan, Birchgrove (AU); Ricardo Bianchi, Sydney (AU)

(73) Assignee: Australian Centre for Advanced Medical Technology Ltd., Sydney (AU)

( * ) Notice: Subject to any disclaimer, the term of this patent is extended or adjusted under 35 U.S.C. 154(b) by 70 days.

(21) Appl. No.: 10/297,366

(22) PCT Filed: Jun. 20, 2001

(86) PCT No.: PCT/AU01/00732

§ 371 (c)(1),
(2), (4) Date: Jun. 10, 2003

(87) PCT Pub. No.: WO01/97691

PCT Pub. Date: Dec. 27, 2001

(65) Prior Publication Data

US 2004/0039294 A1    Feb. 26, 2004

(30) Foreign Application Priority Data

Jun. 22, 2000  (AU) .................................. PQ 8317

(51) Int. Cl.
*A61B 5/02* (2006.01)

(52) U.S. Cl. ..................................................... 600/528

(58) Field of Classification Search ............... 600/500, 600/528, 534; 73/708; 324/457
See application file for complete search history.

(56) References Cited

U.S. PATENT DOCUMENTS

| 4,577,510 A | * | 3/1986 | Bur et al. ..................... 73/708 |
| 4,598,417 A | | 7/1986 | Deno et al. |
| 5,213,108 A | | 5/1993 | Bredsen et al. |
| 5,311,875 A | | 5/1994 | Stasz |
| 5,479,932 A | | 1/1996 | Higgins et al. |
| 5,494,043 A | * | 2/1996 | O'Sullivan et al. ......... 600/500 |
| 5,649,535 A | | 7/1997 | Voith |
| 6,353,324 B1 | * | 3/2002 | Uber et al. ................. 324/457 |
| 6,443,905 B1 | * | 9/2002 | Nissila et al. ............... 600/490 |
| 6,547,743 B2 | * | 4/2003 | Brydon ....................... 600/534 |

FOREIGN PATENT DOCUMENTS

| DE | 38 04 616 A1 | 8/1989 |
| DE | 196 13 261 A1 | 1/1997 |
| WO | WO 97/03600 | 2/1997 |
| WO | WO 99/53277 A1 | 10/1999 |

OTHER PUBLICATIONS

Supplementary European Search report in European Application No. EP 01 94 2906 (counterpart of this application).

* cited by examiner

*Primary Examiner*—George Manuel

(74) *Attorney, Agent, or Firm*—Wood, Phillips, Katz, Clark & Mortimer

(57) ABSTRACT

A biophysical sensor including a sound vibration sensing element (12) to produce a sensed output, and two or more separate signal processing paths to process the sensed outputs to produce output signals. The output signals may reflect specific frequency bands within the raw biological signal. In a further aspect the invention concerns an electronic stethoscope in which the sound vibration sensing element (12) is a PVDF membrane, the signal processing involves an operational amplifier (OP amp) (10) connected to the PVDF membrane, and a unity gain buffer amplifier is connected to the output of the OP amp to allow the connection of headphones directly to the sensor output.

8 Claims, 3 Drawing Sheets

BIOPHYSICAL SENSOR

TECHNICAL FIELD

This invention concerns a biophysical sensor, that is a sensor used to make measurements from animal bodies, in particular humans. In a further aspect the invention concerns an electronic stethoscope.

BACKGROUND ART

ECG measurements require the application of ECG electrodes, and are able to provide "one off" diagnostic information, as well as use over time for patient monitoring. Examination with a stethoscope by a physician or nurse is a "one off" procedure, providing a qualitative, user dependent opinion of sound information.

SUMMARY OF THE INVENTION

This invention is a biophysical sensor including a sound vibration sensing element to produce a sensed output, and two, or more, separate signal processing paths to process the sensed outputs to produce output signals.

The sensor may also include recording and display apparatus to record and display the output signals. The output signals may be two or more of heart sounds, heart movement, breathing movement and breathing sounds. With appropriate recordings, preferably digital, an audio cardiogram can be stored and reviewed. No separate examination with a stethoscope is necessary.

The sensor can be adapted to provide a number of different signal combinations, where combined physical sounds for monitoring patients would be useful. For example, but not exclusively:

Display of heart sounds, at rest, during test procedures eg sleep study or exercise test, and simultaneous measure of foetal heart sounds from the maternal abdomen.

The sensors may be used in a variety of different situation, such as but not exclusively:
1. Display of breathing sounds—monitoring of flow into upper airway and lung regions—indicating occlusion of an endotracheal tube in ICU;
2. Monitoring performance of non-invasive ventilation and CPAP;
3. Emergency evaluation of patients in an ambulance, or the emergency room;
4. Standard routine checks;
5. During anaesthetic;
6. As part of an endotracheal tube;
7. In neonates, and infants where it is important to minimise touch.

The sound sensor may use a PVDF membrane as the sound vibration sensing element. A silver coating on the PVDF may be used to take off electrical signals, and these may include electrode signals as well as signals converted from sound using the piezoelectric effect.

The signal processing may include floating amplifiers mounted on a printed circuit board inside the sensor housing.

A signal processing path may involve an operational amplifier (OPAmp) may be connected to the PVDF membrane. Such an OPAmp may use the intrinsic capacitance of the PVDF together with a resistance to create a high pass filter. Alternatively, or in addition, an OPAmp may be AC coupled directly to the PVDF.

The inclusion of a unity gain buffer amplifier connected to the output of this OPAmp allows the connection of headphones directly to the sensor output, which enables the operator to listen to the heart and breathing sounds. Thus, converting the sensor into an electronic stethoscope.

In a further aspect the invention is an electronic stethoscope, comprising a biophysical sensor including a sound vibration sensing element which uses a PVDF membrane to produce a sensed output, signal processing involving an operational amplifier (OPAmp) connected to the PVDF membrane, and a unity gain buffer amplifier connected to the output of OPAmp to allow the connection of headphones directly to the sensor output.

BRIEF DESCRIPTION OF THE DRAWINGS

Examples of the invention will now be described with reference to the accompanying drawings, in which.

BEST MODES OF THE INVENTION

Figure 1:
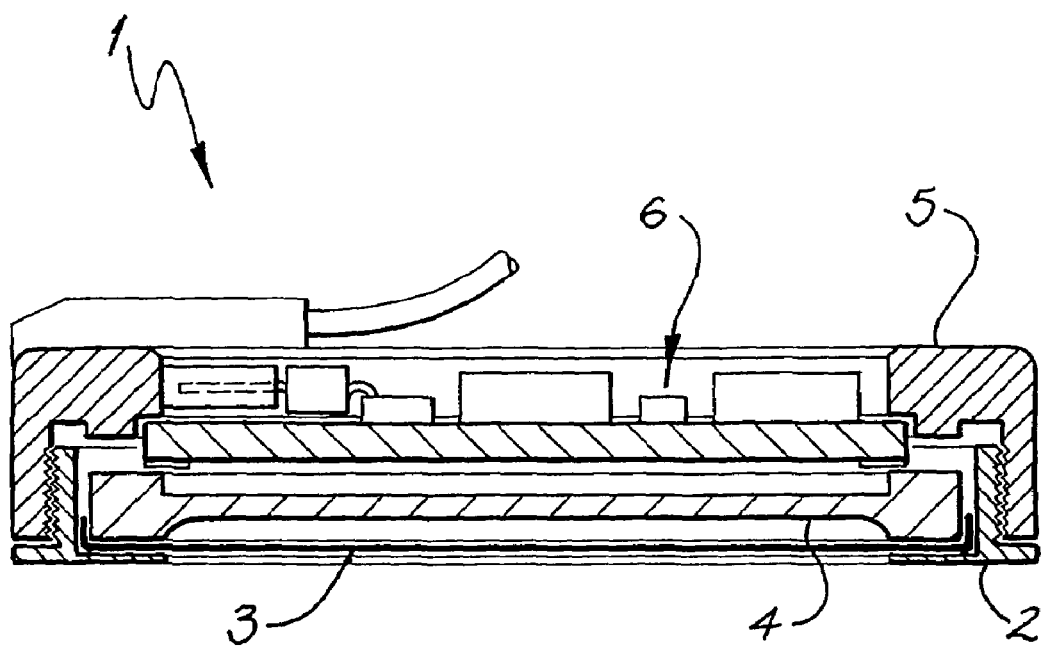
FIG. 1 is a cross-sectional view through a sensor embodying the invention.

Referring to FIG. 1, the acoustic sensor 1 comprises a cylindrical aluminium or plastic body 2 having a diaphragm of PVDF material 3 across its top. The PVDF is a polymer with piezoelectric properties that it uses to generate electrical signals in response to acoustic and pressure signals received. A thin layer of elastogel or other coupling material (not shown) is placed over the top of the sensor, in use, to make contact with a body lying on the bed.

The cylindrical body 2 extends at the top 4 to shield the diaphragm 3, and an aluminium ring 5 locks it in place and provides a live connector. Signals received at the sensor are analysed using built in circuitry mounted on a printed circuit board 6 to provide two or more electronic outputs. The outputs enable the recording and monitoring of signals of different frequency and, of particular significance, widely different amplitude, directly from a single sensor.

The complex signals generated from the patient may incorporate cardiac, respiratory and movement information, and they cause the membrane to vibrate. This vibration produces a weak potential difference across the membrane that is detected, amplified and filtered by the electronics.

The electronics have been mounted immediately adjacent to the membrane, within the sensor housing, using surface-mounted components. This obviates the need for the initial signal (which is in the range of 0 to 10 microvolts) to be conducted out of the sensor to processing electronics via a relatively long cable. Such cabling always causes degradation of the signal due to electromagnetic interference, movement of the cable and power loss due to cable resistance. Thus, no loss of signal is experienced in this way, as the connection is incorporated in the sensor housing.

Figure 2:
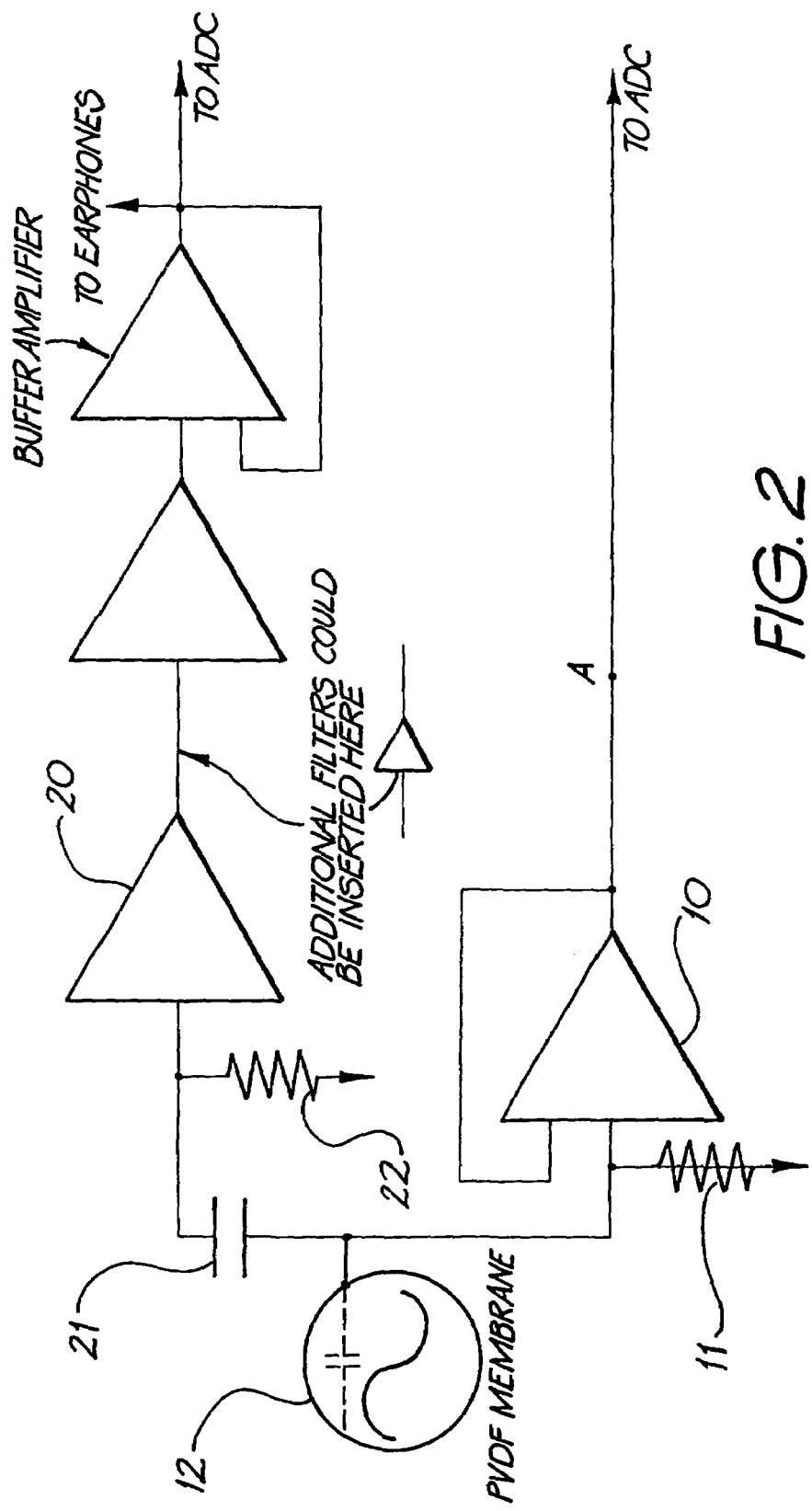
FIG. 2 is a diagram of the internal organisation of the sensor.

The sensor has the ability to transduce a complex biological signal and provide two or more outputs. These outputs are in separate parts of the frequency spectrum of the biological signal and have different amplitudes within that signal. This processing within the sensor is achieved in two stages described below with reference to FIG. 2.

One operational amplifier 10 is connected to the PVDF membrane. By adjusting the resistance 11 connected to the input of the amplifier 10, and using the intrinsic capacitance 12 of the PVDF membrane, a high-pass or wide-band filter can be constructed. OPAmp 10 is a unity gain amplifier that provides an output of the entire signal from nearly DC to several kilohertz. This output, as it is not changed in amplitude, contains information on large-amplitude rhythmic movements of very low frequency, associated with breathing movements. The signal also contains low amplitude, higher frequency information. However, this is not necessary in practice as the amplitude of this higher frequency component is three orders of magnitude less than (i.e. 1000 to 2500 times less than) that of the lower frequency signal.

The second stage involves a second operational amplifier 20 with a gain of >1000. This amplifier is AC coupled directly to the PVDF, by a capacitor 21 with a resistance 22 in parallel chosen to produce a high-pass filter, drawing very little current from the source. This arrangement will remove the large amplitude lower-frequency component of the signal and provide an amplified output (>1000 times) of the relatively weak higher frequency signals that contain information about heart and breathing sounds. Further high and/or low-pass filters can be added to modify the output precisely, however, the amplified signal can be filtered digitally after passing through an analogue to digital converter (ADC). A low pass filter is used to cut the signal above 1000 Hz for input to the ADC.

Figure 3:
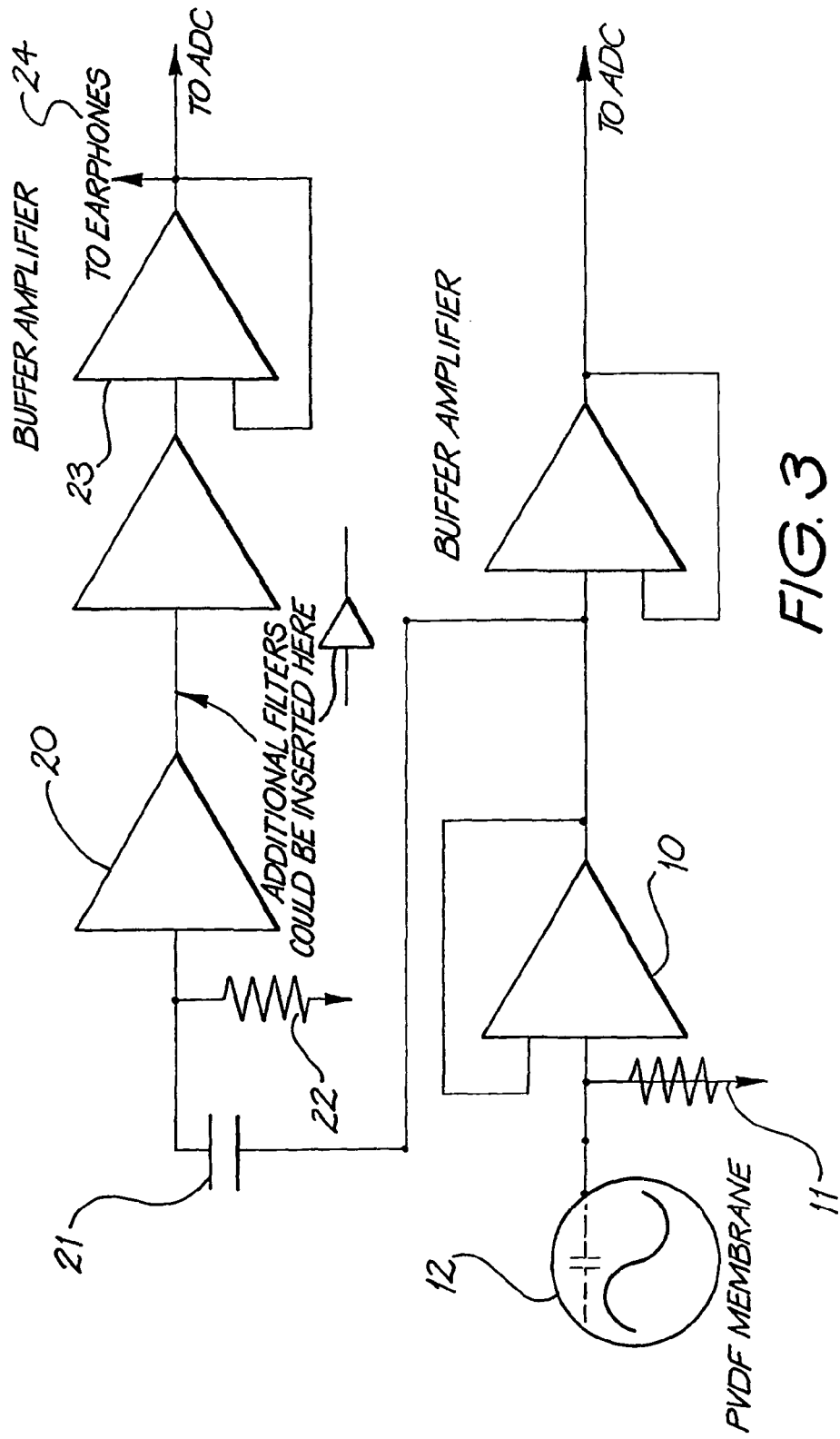
FIG. 3 is a diagram of an alternative internal organisation for the sensor.

In an alternative, the second OPAmp 20 can be coupled to the output of the first OPAmp 10 as shown in FIG. 3. However, in practice the former arrangement reduces noise introduced into the low amplitude signal by sources such as the ADC, to overcome this the output of OPAmp 20 is buffered 23.

This is a basic two-output design, however, by coupling unity gain operational amplifiers to the output of OPAmp 20 with appropriate filtering, multiple outputs can be constructed producing signals reflecting specific frequency bands within the raw biological signal. In each case the sensor filters the raw signal and selectively amplifies low amplitude components, such that, the output of all components within the original signal are at comparable levels.

The inclusion of a unity gain buffer amplifier to buffer the output of this OPAmp 20 allows the connection of headphones directly to the sensor output 24, which enables the operator to listen to the heart and breathing sounds. Thus, converting the sensor into an electronic stethoscope.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A biophysical sensor including a sound vibration sensing element using a PVDF membrane to produce a sensed output, and at least two separate signal processing paths to process the sensed output to produce at least two output signals; where one signal processing path includes an operational amplifier (OP Amp) connected to the PVDF membrane and for amplifying an audible frequency range of the sensed output to an audible amplitude range, and a unity gain buffer amplifier is connected to the output of the OP Amp to allow connection of headphones directly to the sensor output.

2. A biophysical sensor according to claim 1, further including recording and display apparatus to record and display the output signals.

3. A biophysical sensor according to claim 1 or 2, where the output signals are two, or more, of heart sounds, heart movement, breathing movement and breathing sounds.

4. A biophysical sensor according to claim 1, where a silver coating on the PVDF membrane is used to take off electrical signals.

5. A biophysical sensor according to claim 1, where the signal processing includes floating amplifiers mounted on a printed circuit board inside the sensor housing.

6. A biophysical sensor according to claim 1, where the OPAmp uses the intrinsic capacitance of the PVDF together with a resistance to create a high pass filter.

7. A biophysical sensor according to claim 6, where alternatively, or in addition, an OPAmp is AC coupled directly to the PVDF membrane.

8. An electronic stethoscope, comprising a biophysical sensor including a sound vibration sensing element which uses a PVDF membrane to produce a sensed output, signal processing involving an operational amplifier (OPAmp) connected to the PVDF membrane and for amplifying an audible frequency range of the sensed output to an audible amplitude range, and a unity gain buffer amplifier connected to the output of the OPAmp to allow connection of headphones directly to the sensor output.

* * * * *